US00PP12743P2

(12) United States Plant Patent
Heil

(10) Patent No.: US PP12,743 P2
(45) Date of Patent: Jul. 2, 2002

(54) CARNATION PLANT NAMED 'SUNFLOR TRITON'

(75) Inventor: Jacob Johannes Heil, Aalsmeer (NL)

(73) Assignee: P. Kooij & Zinn B.V., Aalsmeer (DE)

( * ) Notice: Subject to any disclaimer, the term of this patent is extended or adjusted under 35 U.S.C. 154(b) by 0 days.

(21) Appl. No.: 09/379,262

(22) Filed: Aug. 23, 1999

(51) Int. Cl.[7] ..... A01H 5/00
(52) U.S. Cl. ..... Plt./278
(58) Field of Search ..... Plt./278, 283, 273, Plt./272

(56) References Cited

PUBLICATIONS

GTITM UPOVROM Citation for 'Sunflor Triton' as per NL PBR ANJ2039; Jun. 18, 1993.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Carnation plant named 'Sunflor Triton', characterized by its very large purple red-colored flowers; upright and mounded plant habit; good basal branching with about 10 lateral branches developing after pinching; rapid growth rate; fragrant flowers, and good postproduction longevity.

1 Drawing Sheet

BACKGROUND OF THE INVENTION

The present invention relates to a new and distinct cultivar of Carnation plant, botanically known as *Dianthus caryophyllus* and hereinafter referred to by the cultivar name 'Sunflor Triton'.

The new Carnation is a product of a planned breeding program conducted by the Inventor in Aalsmeer, The Netherlands. The objective of the breeding program is to develop new compact Carnation cultivars suitable for container production with attractive flower color and early flowering.

The new Carnation originated from a cross made by the Inventor of the *Dianthus caryophyllus* cultivar 'Rosso', not patented, as the female, or seed, parent with the *Dianthus caryophyllus* cultivar 'D. Japan', not patented, as the male, or pollen, parent. The cultivar 'Sunflor Triton' was discovered and selected by the Inventor as a flowering plant within the progeny of the stated cross in a controlled environment in Aalsmeer, The Netherlands, in 1991.

Asexual reproduction of the new cultivar by terminal cuttings taken at Aalsmeer, The Netherlands, has shown that the unique features of this new Carnation are stable and reproduced true to type in successive generations of asexual reproduction.

SUMMARY OF THE INVENTION

The following traits have been repeatedly observed and are determined to be the unique characteristics of 'Sunflor Triton'. These characteristics in combination distinguish 'Sunflor Triton' as a new and distinct cultivar:

1. Very large purple-red colored flowers.

1. Upright and mounded plant habit.

3. Good basal branching with about 10 lateral branches developing after pinching.

4. Rapid growth rate.

5. Fragrant flowers.

6. Good postproduction longevity.

Plants of the new Carnation are taller and have larger flowers than plants of the female parent, the dark red-flowered cultivar 'Rosso'. Plants of the new Carnation are more compact, flower earlier and have larger flowers than plants of the male parent, the pink-flowered cultivar 'D. Japan'.

The new Carnation can be compared to the cultivar 'Sunflor Surprise' (U.S. Plant patent application Ser. No. 09/379,263). However, in side-by-side comparisons conducted by the Inventor in Aalsmeer, The Netherlands, plants of the new Carnation differ from plants of the cultivar 'Sunflor Surprise' in the following characteristics:

1. Plants of the new Carnation are larger, grow faster and flower earlier than plants of the cultivar 'Sunflor Surprise'.

2. Plants of the new Carnation have larger flowers than plants of the cultivar 'Sunflor Surprise'.

3. Plants of the new Carnation and the cultivar 'Sunflor Surprise' differ in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plants of 'Sunflor Triton'. Flower and foliage colors in the photograph may appear different from the acutal colors due to light reflectance.

DETAILED BOTANICAL DESCRIPTION

The cultivar 'Sunflor Triton' has not been observed under all possible environmental conditions. The phenotype may vary somewhat with variations in environment such as temperature and light intensity, without, however, any variance in genotype. The following observations, measurements and comparisons describe plants grown in 9-cm pots in Aalsmeer, The Netherlands, under conditions approximating commercial practice in a glass-covered greenhouse with day and night temperatures averaging about 20 and 14° C., respectively. Plants used for the description and photographs were about 10 weeks old.

In the following description, color references are made to The Royal Horticultural Society Colour Chart except where general terms of ordinary dictionary significance are used.

Botanical classification: *Dianthus caryophyllus* 'Sunflor Triton'.

Parentage:

*Male parent.*—*Dianthus caryophyllus* cultivar 'D. Japan', not patented.

*Female parent.*—*Dianthus caryophyllus* cultivar 'Rosso', not patented.

Propagation:

*Type.*—Terminal cuttings.

*Time to initiate roots.*—About 5 days during the summer and about 7 days during the winter.

*Time to develop roots.*—About 20 days during the summer and about 28 days during the winter.

*Root description.*—Fine, freely-branching.

Plant description:

*Plant form.*—Upright and mounded; inverted triangle.

*Growth and branching habit.*—Good branching with about ten lateral branches developing after pinching, dense and bushy growth. Appropriate for 9-cm and larger containers.

*Vigor.*—Vigorous.

*Growth rate.*—Rapid growth rate; starting with a plant grown in a 5-cm container, about 10 weeks are required to produce a flowering plant in a 15-cm container.

*Plant height.*—About 15 cm.

*Plant width.*—About 17 cm.

*Lateral branches.*—Length: About 12 cm. Diameter: About 2 mm. Internode length: About 3 cm.

Color: 139A.

*Foliage description.*—Leaves simple; symmetrical; abundant; opposite; sessile. Quantity of leaves per lateral branch: About 24. Length: About 6 cm. Width: About 6 mm. Shape: Linear; apex, acute; base, cordate; margin, entire. Texture: Smooth, glabrous; waxy. Color: Young foliage, upper surface: 138B. Young foliage, lower surface: 138B. Fully expanded foliage, upper surface: 138A. Fully expanded foliage, lower surface: 138A. Venation, upper surface: 138A. Venation, lower surface: 138A.

Flower description:

*Flower type and habit.*—Purple red-colored double flowers. Freely and continuously flowering. Usually about three flowers per lateral branch; typically about 25 open flowers per plant. Flowers flat and convex. Flowers positioned mostly above the foliage; typically facing upright or outward. Flowers persistent.

*Flowering season.*—Year-round under greenhouse conditions. In the garden, flowering is continous during the summer.

*Flower longevity.*—About two weeks on the plant.

*Fragrance.*—Moderately strong, clove-like fragrance typical of the species.

*Flower size.*—Diameter: About 4 cm. Depth: About 4 cm.

*Flower buds.*—Length: About 1.5 cm. Diameter: About 8 mm. Shape: Elliptic. Color: 144A. Rate of opening: About one week.

*Petals/petaloids.*—Quantity: About 25, overlapping. Length: About 3.5 cm. Width: About 1.7 cm. Shape: Mostly rounded; apex, acute; margin, serrated; base, attenuate. Texture: Rippled, dull. Color: When opening and fully opened, upper surface: Purple red, 63A. When opening and fully opened, lower surface: Lighter purple red, 63B.

*Sepals.*—Quantity: Five. Calyx length: About 1.8 cm. Calyx width: About 1.1 cm. Shape: Triangular; apex, rounded; margin, entire. Texture: Smooth, glossy. Color: Upper surface: 145B. Lower surface: 138A.

*Peduncles.*—Length: About 3 mm. Angle: Erect. Strength: Strong. Color: 138A.

*Reproductive organs.*—Androecium: Stamen number: Up to ten. Anther length: About 1 mm. Anther shape: Oblong. Anther color: 4D. Amount of pollen: Scarce. Pollen color: Yellow. Gynoecium: Pistil number: One. Pistil length: About 1.7 cm. Style length: About 1.3 cm. Style color: 4D. Stigma color: 63A. Ovary color: 144B.

*Seed.*—Size: About 2 by 2 mm. Color: Close to 202A.

Disease resistance: Under commercial conditions, resistance to pathogens common to Dianthus has not been observed.

It is claimed:

1. A new and distinct cultivar of Carnation plant named 'Sunflor Triton', as illustrated and described.

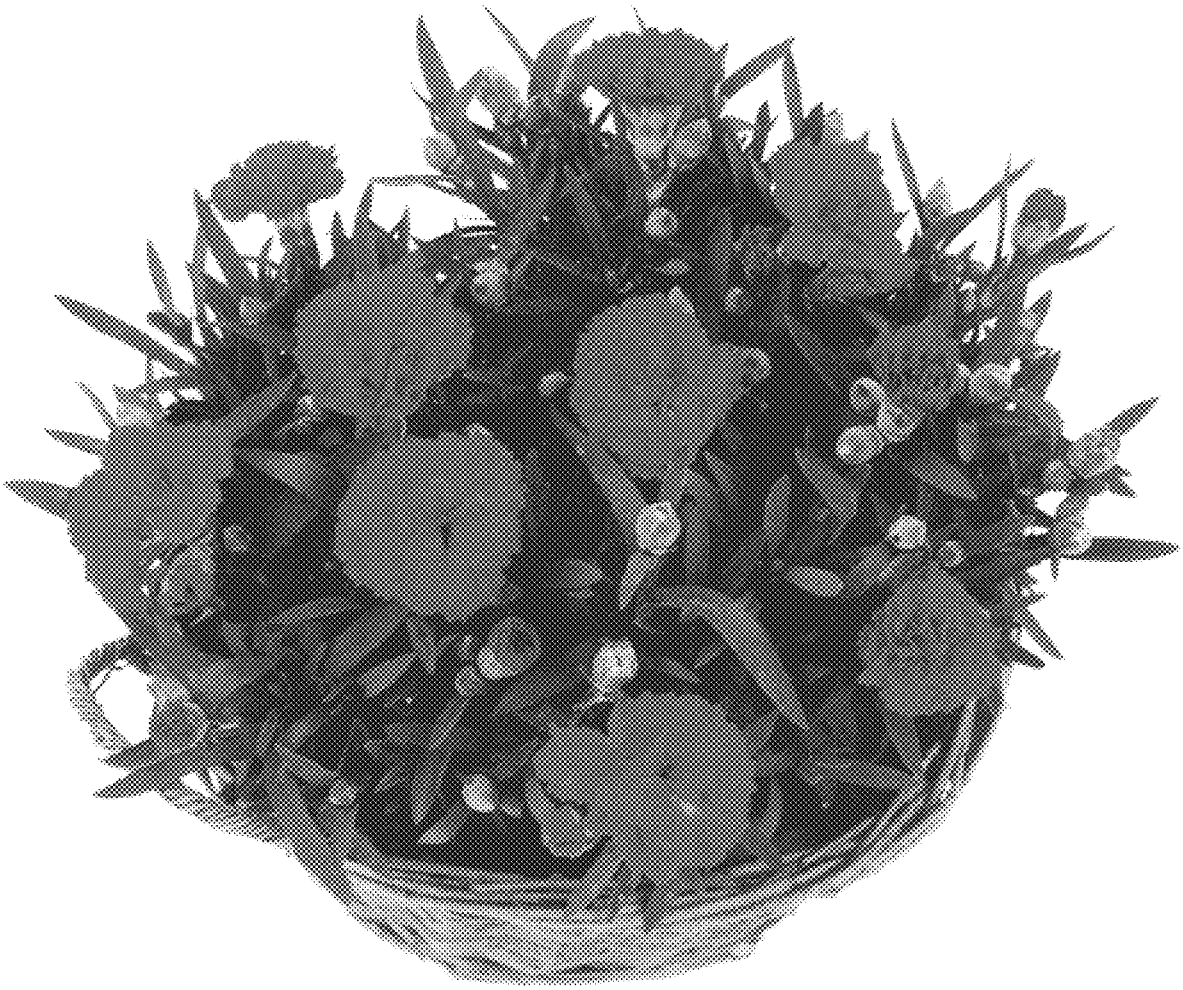

* * * * *